(12) United States Patent
Boiten et al.

(10) Patent No.: US 6,322,594 B1
(45) Date of Patent: Nov. 27, 2001

(54) HIP JOINT FOR AN ARTIFICIAL LEG

(75) Inventors: Herman Boiten, Amersfoort (NL); Helmut Wagner, Duderstadt (DE)

(73) Assignee: Otto Bock Orthopaedische Industrie Besitz-und Verwaltungs-Kommanditgesellschaft, Duderstadt (DE)

( * ) Notice: Subject to any disclaimer, the term of this patent is extended or adjusted under 35 U.S.C. 154(b) by 0 days.

(21) Appl. No.: 09/627,313

(22) Filed: Jul. 27, 2000

(30) Foreign Application Priority Data

Jul. 27, 1999 (DE) .............................. 199 35 203

(51) Int. Cl.⁷ ....................................... A61F 2/32
(52) U.S. Cl. ........................ 623/27; 623/22.11; 623/43
(58) Field of Search .................. 623/27, 43, 44, 623/45, 22.11

(56) References Cited

U.S. PATENT DOCUMENTS

| | | | |
|---|---|---|---|
| 3,663,967 | 5/1972 | Vermillion | 3/15 |
| 4,215,441 | 8/1980 | Wilson | 3/15 |
| 4,488,320 | 12/1984 | Wilson | 3/15 |
| 4,513,457 | 4/1985 | Glabiszewski | 3/15 |
| 4,904,270 | 2/1990 | Cooper | 623/38 |
| 4,911,709 * | 3/1990 | Marlow et al. | 623/39 |
| 5,746,774 * | 5/1998 | Kramer et al. | 623/39 |
| 5,800,567 * | 9/1998 | Cooper et al. | 623/39 |
| 5,948,021 * | 9/1999 | Radcliffe | 623/44 |
| 6,187,052 * | 2/2001 | Molino et al. | 623/52 |

FOREIGN PATENT DOCUMENTS

| | | |
|---|---|---|
| 311 462 | 3/1919 | (DE) . |
| 0 093 867 | 6/1986 | (EP) . |
| 0 258 328 | 7/1991 | (EP) . |

OTHER PUBLICATIONS

Naeder et al., Otto Bock Prothesen–Kompendium, Prothesen fuer die untere Extremitaet, Schiele & Schoen, 1987, pp. 28–31, 66–71, 88–91.

* cited by examiner

Primary Examiner—Bruce Snow
(74) Attorney, Agent, or Firm—Foley & Lardner

(57) ABSTRACT

The invention relates to a hip joint which has an attachment for an artificial leg and which, in order to permit a largely natural walking movement, has the following features: a front link (5) and a rear link (6) are articulated at their respective upper sections, via a first joint connection (1) and a second joint connection (2), respectively, to a front section and a rear section, respectively, of an upper transverse link (7), and are articulated at their respective lower sections, via a third joint connection (3) and a fourth joint connection (4), respectively, to a front section and a rear section, respectively, of a lower transverse link (8); the first and third joint connections (1, 3) together have at least five degrees of freedom; the second joint connection (2) is a hinge pin which with its pivot axis (2a) is approximately perpendicular to the sagittal plane and has one degree of freedom; the fourth joint connection (4) has a pivot axis (4a) with mediolateral and anteroposterior inclination and with one degree of freedom, so that a swiveling about the pivot axis (2a) of the second joint connection (2) causes outward/inward swiveling and abduction/adduction of the lower transverse link (8).

11 Claims, 10 Drawing Sheets

HIP JOINT FOR AN ARTIFICIAL LEG

BACKGROUND OF THE INVENTION

The present invention relates to a hip joint for an artificial leg. The upper side of the hip joint has connection means for attachment to a prosthesis basket, and the underside of the hip joint is designed for releasable attachment to the artificial leg. An extension limit stop defines the starting position of the hip joint in extension.

Such an embodiment can be found in EP 0,093,867 B1. In this previously disclosed hip joint, a first joint part screwed to a connection means is connected via a pivot joint to a second joint part provided for connection to the artificial leg. The pivoting movement of the second joint part is limited by stops for the standing and sitting positions of the artificial leg. The hip joint is designed with one axis and accordingly has only one degree of freedom, and the second joint part and the artificial leg connected to it can swivel in only one plane. By contrast, the very much more complicated movement of a natural hip joint takes place in three planes.

Another design comparable to the hip joint described above is disclosed in EP 0,285,328 B1.

SUMMARY OF THE INVENTION

The main object of the invention is to develop a hip joint of the above-mentioned structural type that is adapted more to the natural pattern of hip and leg movement and thus permits as comfortable a gait as possible.

In accomplishing the foregoing and other objects, there has been provided according to the present invention a hip joint for connecting an artificial leg to a prosthesis mounting part, the hip joint comprising:

an upper transverse link having on its upper side a connector for attachment to a prosthesis mounting part:

a lower transverse link having on its underside a connector for releasable attachment to an artificial leg;

a front link articulated at its upper section, via a first joint, to a front section of the upper transverse link and articulated at its lower section, via a third joint connection, to a front section of the lower transverse link, wherein the first and third joint connections together have at least five degrees of freedom;

a rear link articulated at its upper section, via a second joint connection, to a rear section of the upper transverse link and at its lower section, via a fourth joint connection, to a rear section of the lower transverse link, wherein the second joint connection comprises a hinge pin having its pivot axis approximately perpendicular to the sagittal plane and has one degree of freedom, and wherein the fourth joint connection has a pivot axis with mediolateral and anteroposterior inclination with respect to the sagittal plane and has one degree of freedom, whereby a swiveling about the pivot axis of the second joint connection causes outward/inward swiveling and abduction/adduction of the lower transverse link; and an extension limit stop defining the starting position of the hip joint in extension.

Further objects, features and advantages of the invention will become apparent from the detailed description of preferred embodiments that follows, when considered in conjunction with the accompanying figures of drawing.

DETAILED DESCRIPTION OF PREFERRED EMBODIMENTS

To influence the kinematics of the joint, it is preferable if the length of the front link or the distance between the first and third joint connections can be adjusted to suit the person using the prosthesis. Outward rotation and abduction are changed by presetting a fairly substantial length for the front link. In a modified embodiment, it is also possible for the front link to be elastic in the direction of tension.

Starting from the extension position (0° position), a rearward movement of the leg is a hyperextension. The rotation which occurs during hyperextension and flexion in the transverse and frontal plane approximates the natural movement of the: hip. This reduces the loading of the artificial leg by torsional moments. As a result of the easier gait achieved by this means, less energy is expended for walking. In addition, the hip joint designed according to the invention permits a comfortable sitting position.

The extension limit stop can be designed to be rigid or, alternatively, elastically resilient. Thus, the extension position can be defined by the length of a spring forming the extension limit stop. If the extension limit stop is intended to permit a hyperextension, it can expediently be designed as a storage spring. The action on the optionally pre-tensioned storage spring then begins in the extension position (0° position seen in the sagittal plane) and increases up to the maximum hyperextension; after knee flexion, the storage spring then relaxes, its relaxation ending when the extension position (0° flexion) is reached. Thus, energy is stored in the extension limit stop designed as a storage spring in hyperextension, which energy is again released at the start of the swing phase and is used up on reaching the extension position (0° position).

Figure 2:
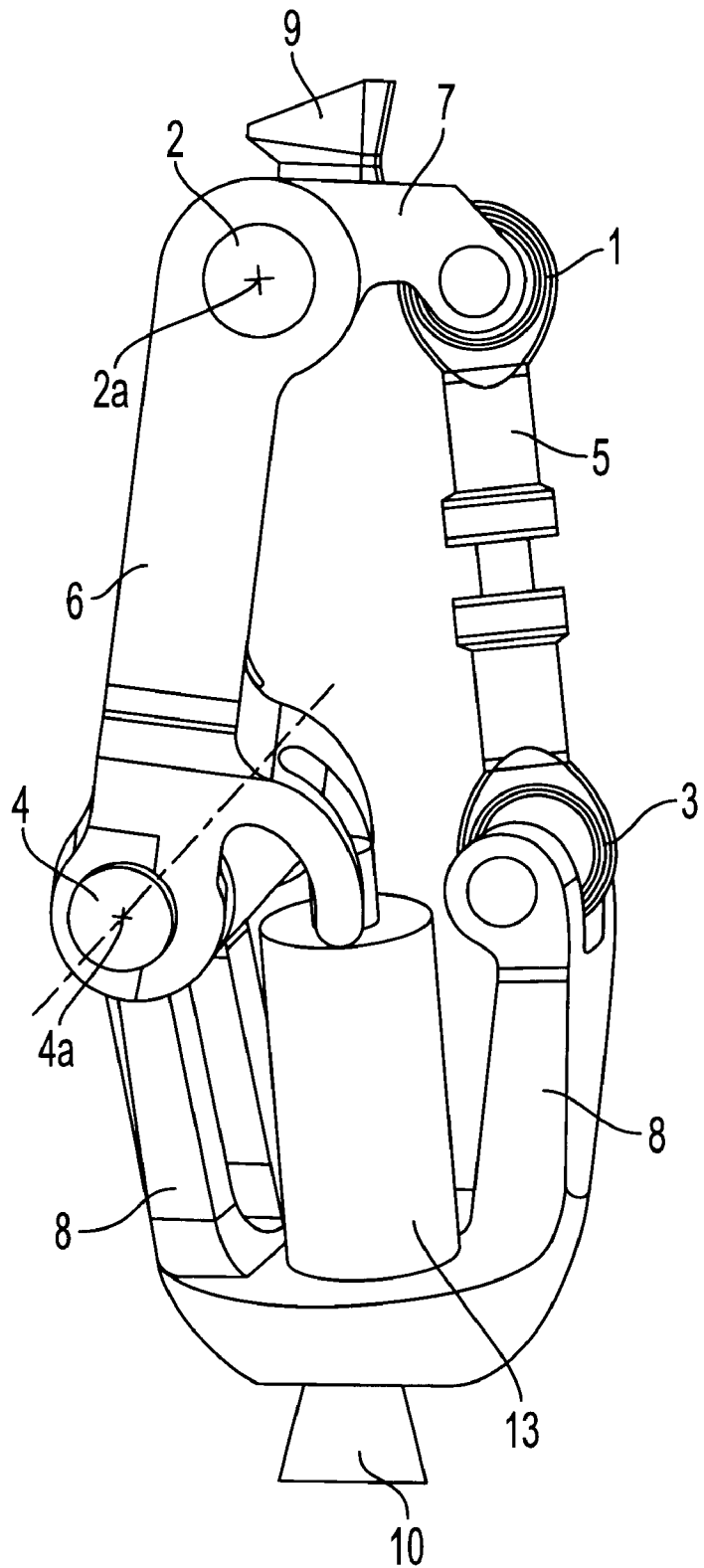
FIG. 2 shows a left hip joint in a sagittal view in the extension position (0° position)
Figure 3:
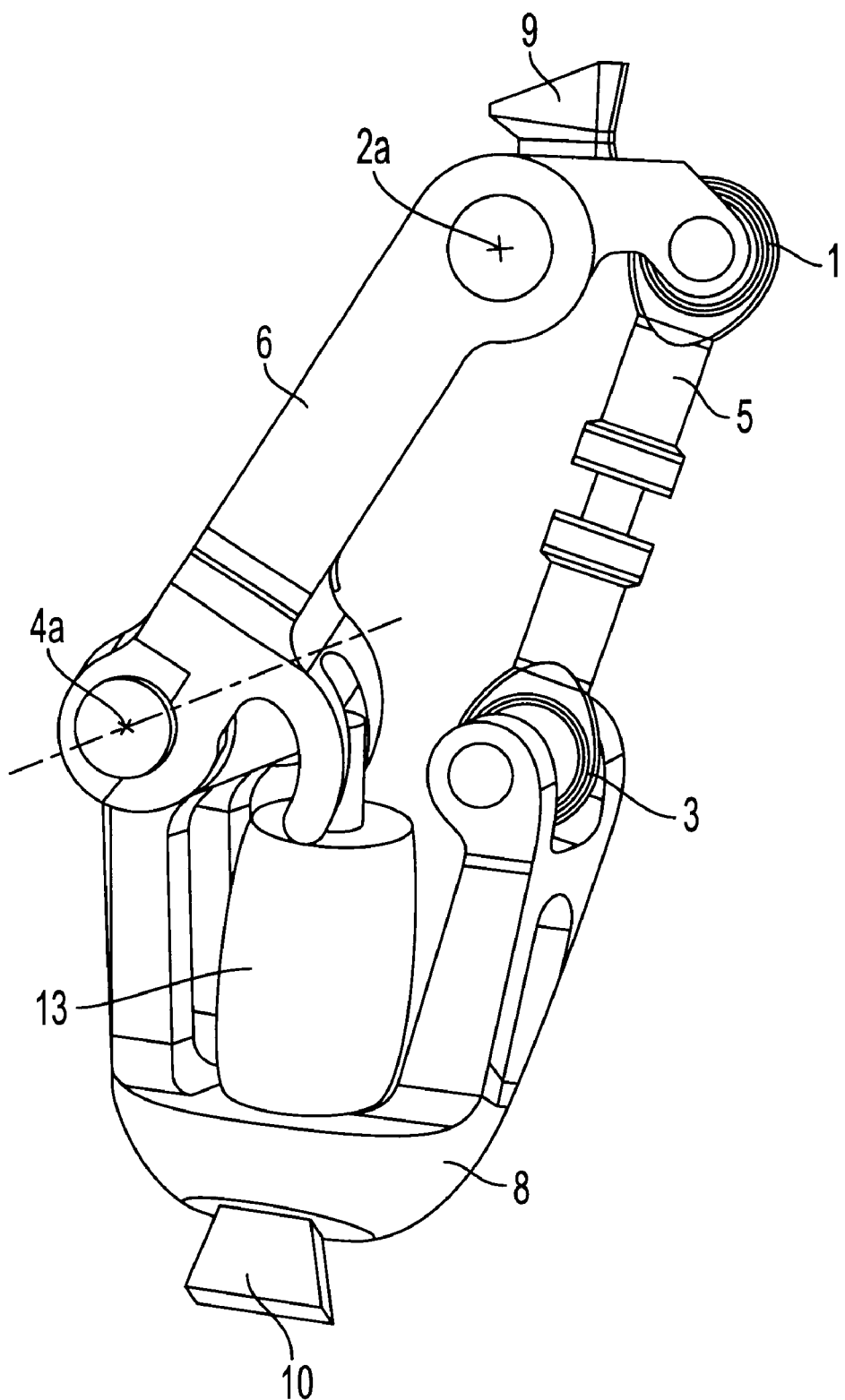
FIG. 3 shows the hip joint according to FIG. 2 in a sagittal view at 10° hyperextension.
Figure 4:
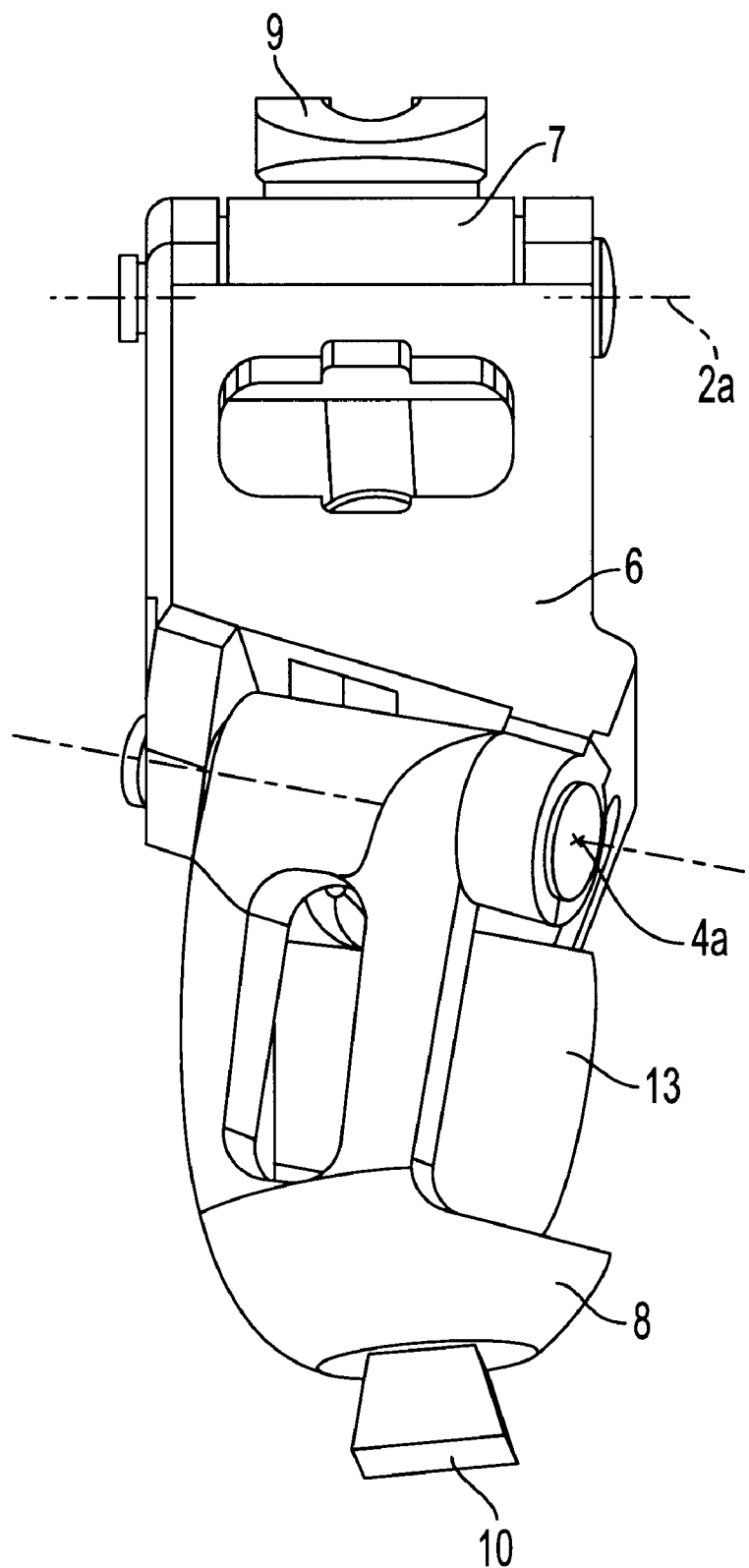
FIG. 4. shows the representation according to FIG. 3 in a rear view.

The hip-joint shown in FIG. 2 has four joint connections 1, 2, 3, 4 and overall one degree of freedom. A front link 5 and a rear link 6 are articulated at their respective upper ends, via the first joint connection 1 and the second joint connection 2, respectively, to a front section and a rear section, respectively, of an upper transverse link 7. Front link 5 and rear link 6 are articulated at their respective lower ends, via the third joint connection 3 and the fourth joint connection 4, respectively, to a front section and a rear section, respectively, of a lower transverse link 8. The length of the front link 5 or the distance between the first and third joint connections can be adjusted to suit the person using the prosthesis, for example, by including an adjustment mechanism for varying the length of front link 5, as illustrated in FIG. 2.

Figure 1:
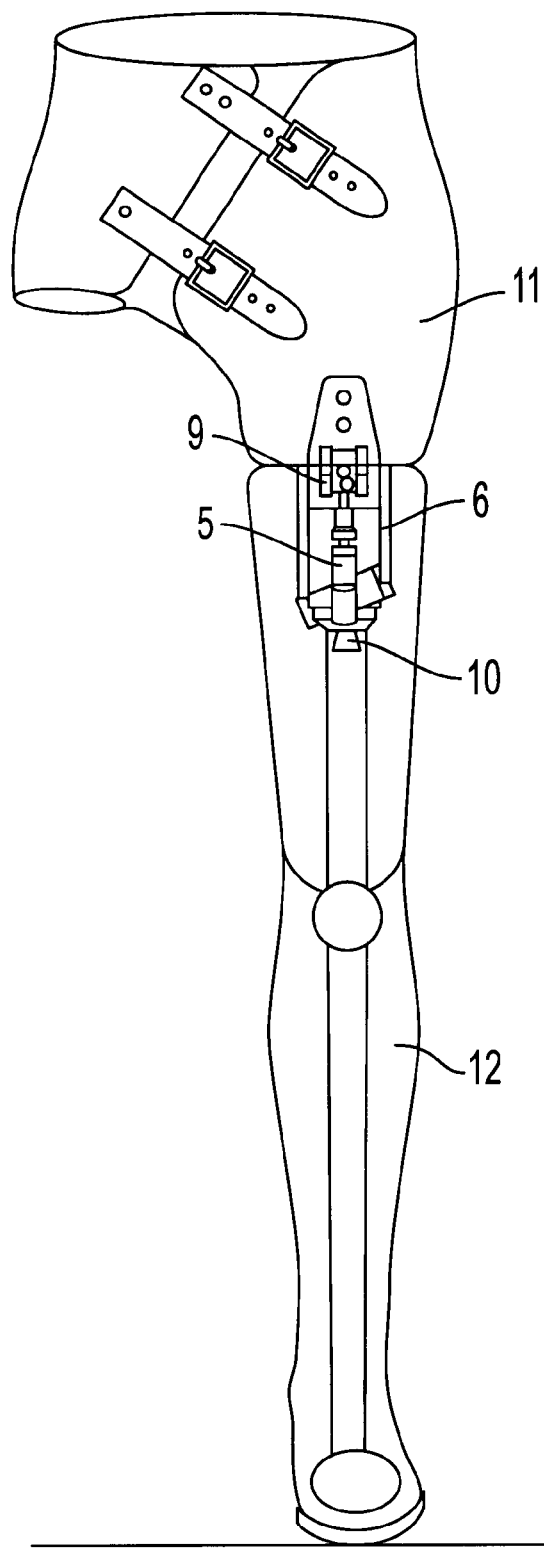
FIG. 1 shows, in diagrammatic representation, a front view of a left artificial leg connected via a hip joint to a prosthesis basket.

The upper transverse link 7 is provided with a connector 9 for attachment to a prosthesis basket 11, and the lower transverse link 8 is provided with an adapter 10 for releasable attachment to an artificial leg 12 (see also FIG. 1).

Figure 9:
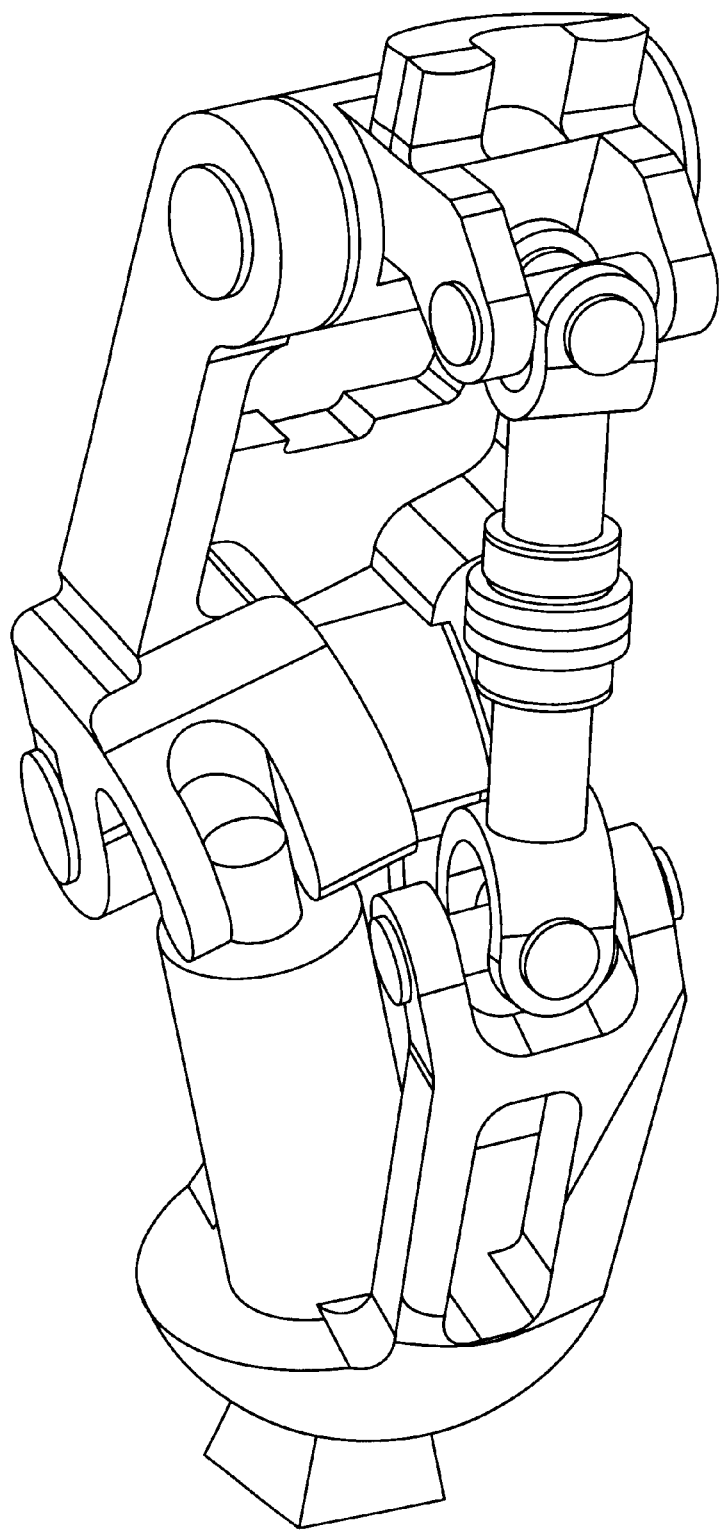
FIG. 9 is a perspective view showing an alternative embodiment of the invention employing two cardan joints.
Figure 10:
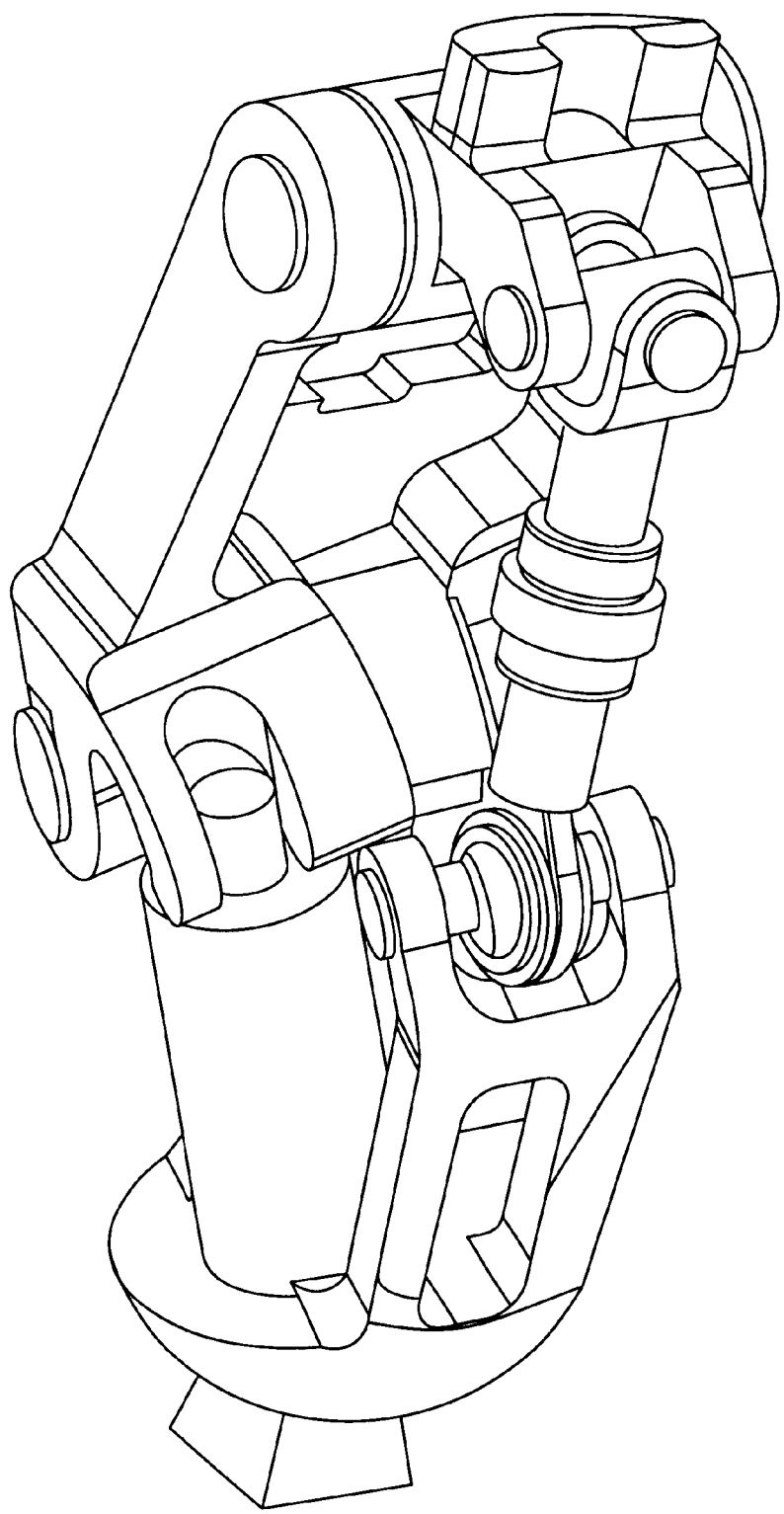
FIG. 10 is a perspective view showing yet another embodiment of the invention employing one ball joint and one cardan joint.

The first and third joint connections 1, 3 together have at least five degrees of freedom and can each be formed either by a spherical joint, as shown, or, alternatively, by a cardan joint. In the latter case, an additional pivot connection is necessary and this is preferably formed by a front link 5 that can pivot about its longitudinal axis and connects the two cardan joints to each other (FIG. 9). A combination of a spherical joint and a cardan joint is also possible (FIG. 10).

The second joint connection 2 is formed by a hinge pin that, with its pivot axis 2a, is approximately perpendicular to the sagittal plane and has one degree of freedom.

The fourth joint connection 4 has a pivot axis 4a with mediolateral and anteroposterior inclination and with one degree of freedom, so that a swiveling of the lower transverse link 8 about this pivot axis 4a in the clockwise direction causes an outward swiveling of the attached artificial leg 12 with outwardly directed abduction, while swiveling counterclockwise causes an inward swiveling and adduction. Seen from the front, the lateral end of the pivot axis 4a thus lies higher than the medial end, and seen from the front this inclination is approximately 17.5°. This inclination mainly influences the outward and inward rotation.

Seen from above, the lateral end of the pivot axis 4a lies further to the front, and the medial end thus further to the rear, and this skewed position is preferably approximately 17° and mainly influences the abduction/adduction. In normal walking, this embodiment leads to a maximum outward rotation of the artificial leg of approximately 10° and to a maximum abduction of approximately 5°. During hip extension, the hip joint thus leads to a decreasing abduction, as a result of which the foot comes closer beneath the center of gravity of the body.

Figure 5:
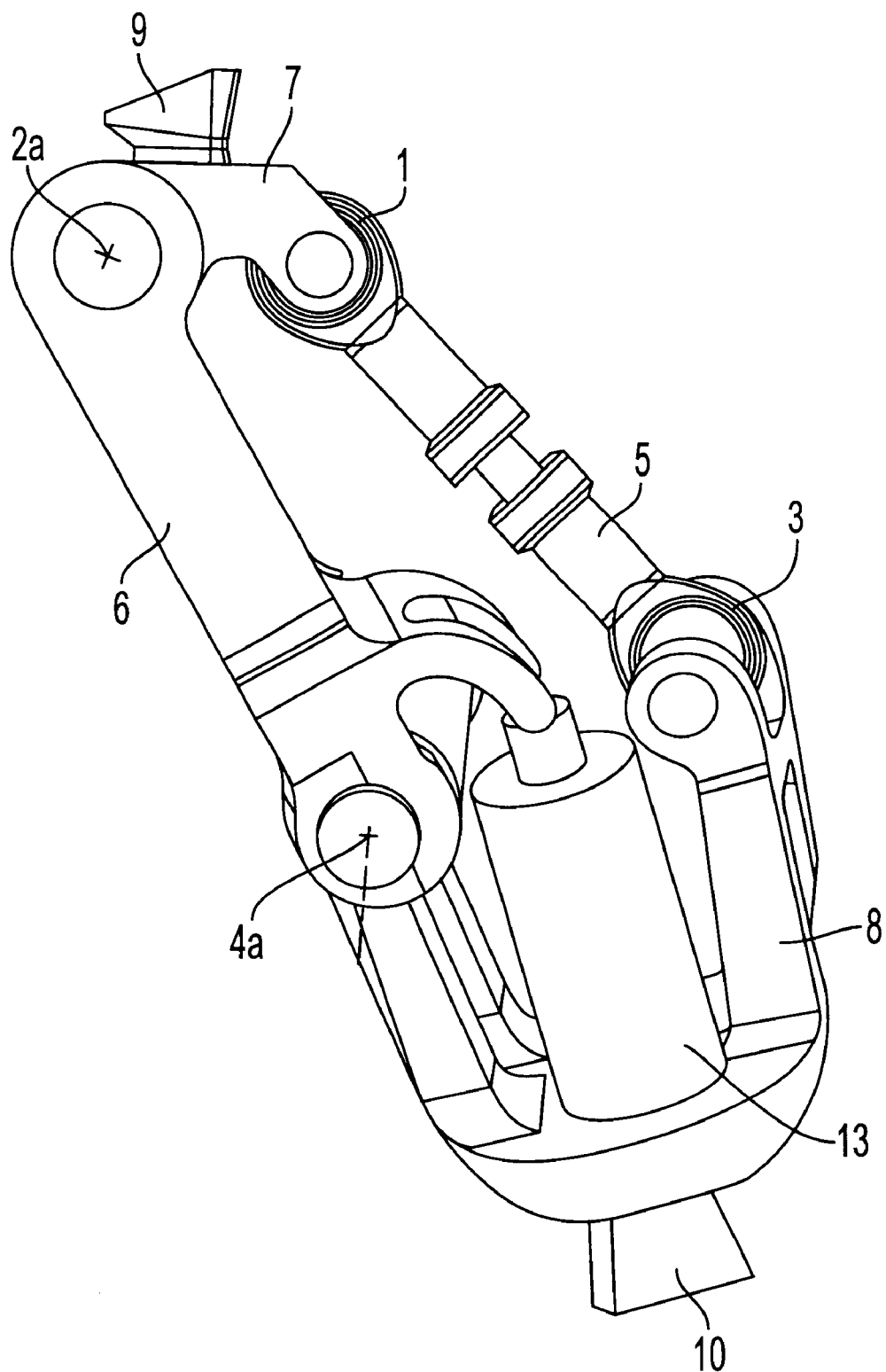
FIG. 5 shows the hip joint according to FIG. 2 in a sagittal view at 20° flexion.
Figure 6:
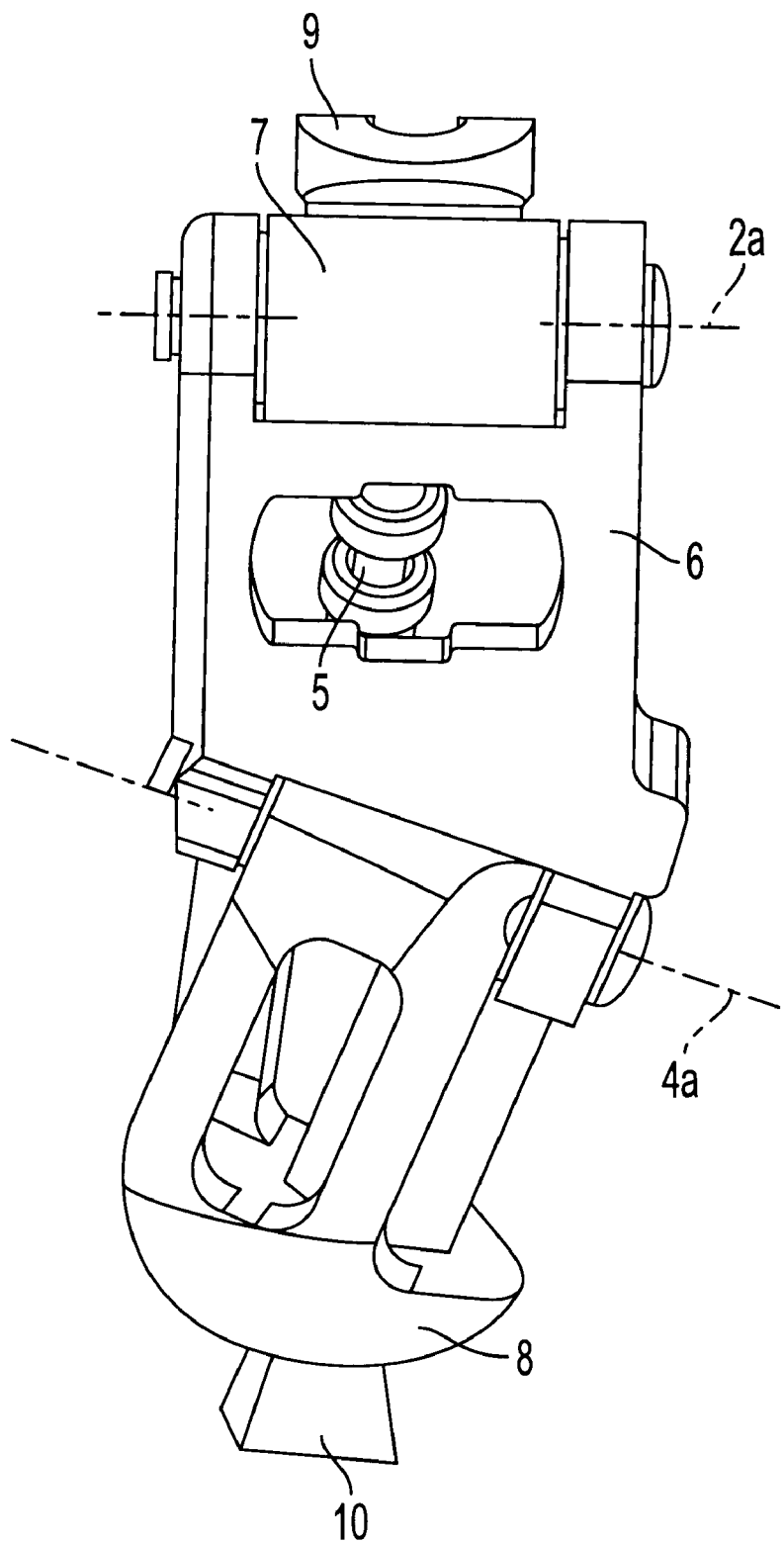
FIG. 6 shows the representation according to FIG. 5 in a rear view.
Figure 7:
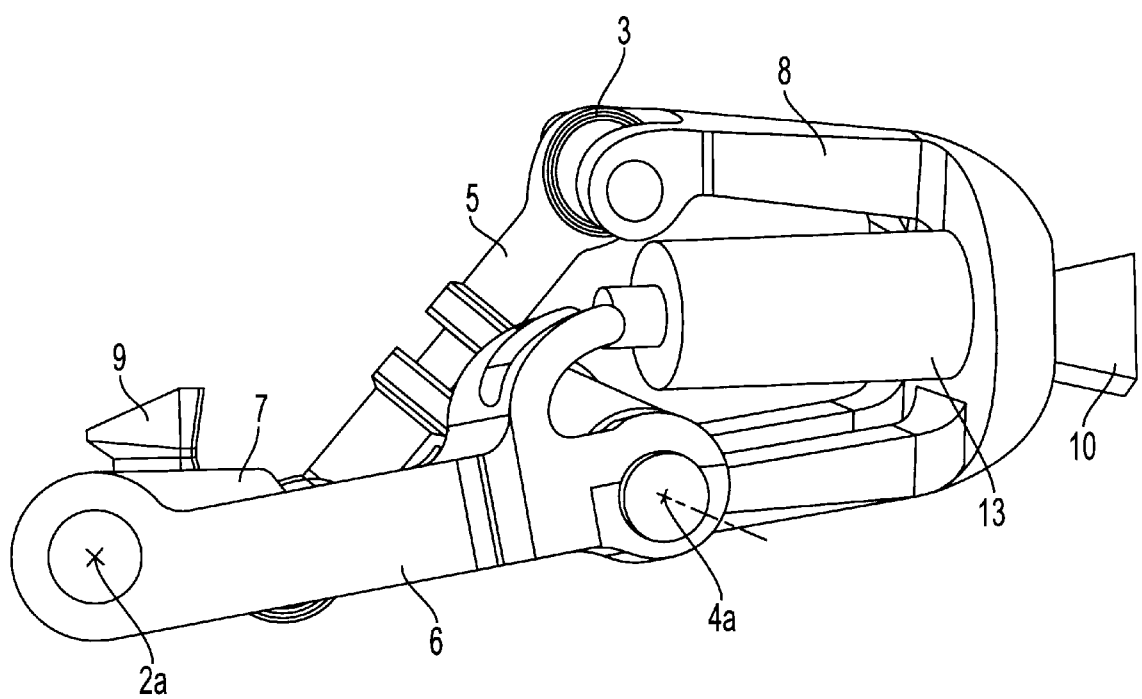
FIG. 7 shows the hip joint according to FIG. 2 in a sagittal view at 90° flexion.
Figure 8:
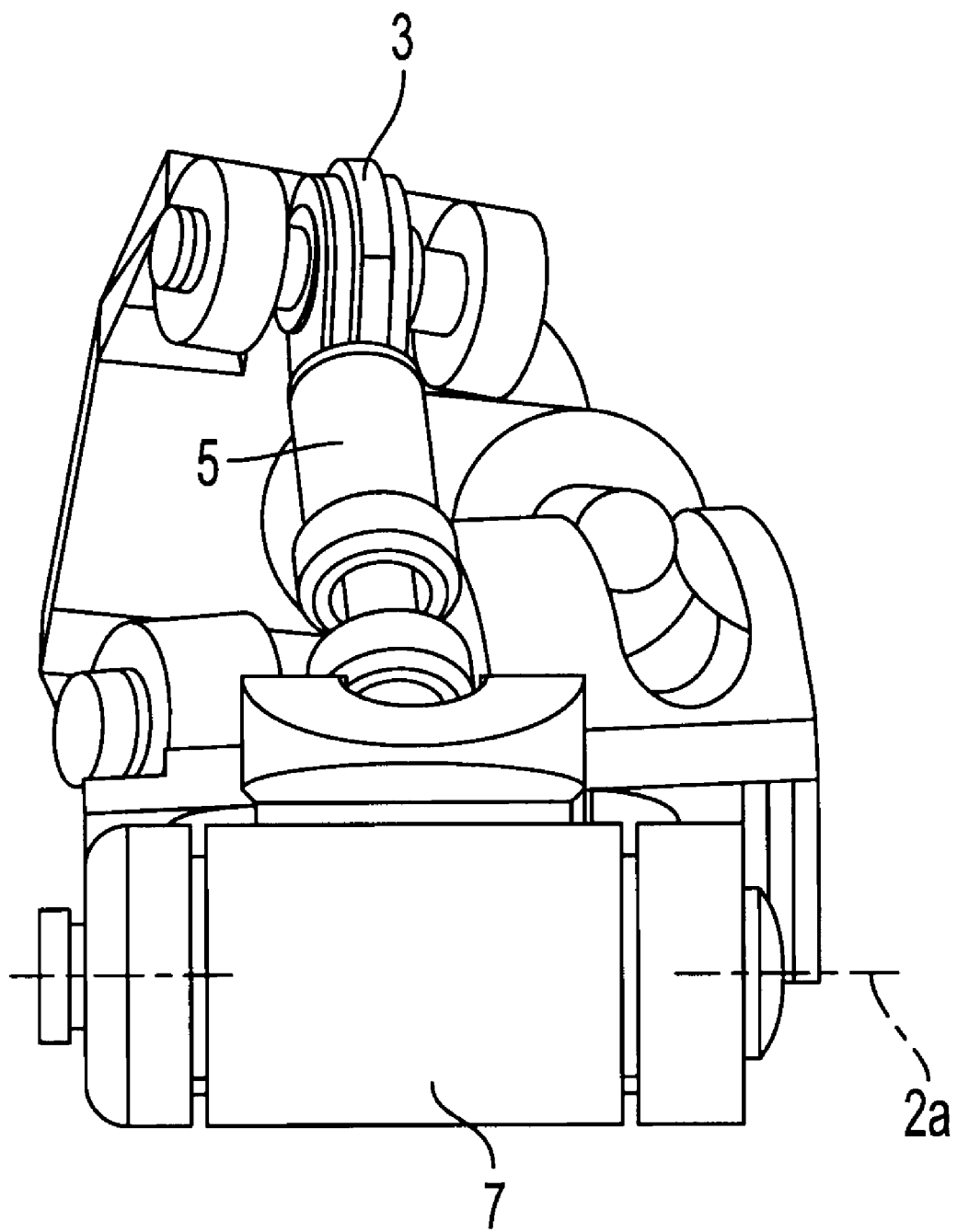
FIG. 8 shows the representation according to FIG. 7 in a rear view.

In the representation according to FIG. 2, a swiveling of the lower transverse link 8 about the pivot axis 4a in the clockwise direction causes a flexion of the artificial leg 12. (FIG. 5) If, after a given flexion, further swiveling in the clockwise direction is no longer possible, the direction of the swiveling reverses, in other words goes counterclockwise upon further flexion. In this way, the outward swiveling and abduction decrease, as a result of which a normal seating position is reached. (FIG. 7) In other words, a swiveling of the rear link 6 about the pivot axis 4a in the counterclockwise direction leads to an increase in the angle between rear link 6 and lower transverse link 8. This angle reaches a maximum and subsequently decreases again. After further increase of the flexion angle of the whole hip joint, the angle enclosed between rear link 6 and lower transverse link 8 once again reaches approximately its starting value, corresponding to the seating position, in which the artificial leg has a slight abduction and outward rotation.

The hip-joint shown in FIG. 2 moreover has an extension limit stop 13 which defines the starting position of the hip joint at 0°, that is to say the extension position. The extension limit stop 13 is preferably made of a resilient material, as shown, which can function as a storage spring. The length of extension limit stop 13 defines the extension position, as shown in FIG. 2.

A limit stop for limiting the swing phase can also be provided. The hip joint can further be fitted with a damping means.

It will be appreciated by those skilled in this art that the present invention can take the form of other embodiments that embody the basic principles of the invention, as illustrated by example above. It is intended that the accompanying claims will cover all such obvious modifications and equivalents of the disclosed subject matter.

The entire disclosure of German Patent Application No. 199 35 203.8, filed Jul. 27, 1999, is hereby incorporated by reference.

What is claimed is:

1. A hip joint for connecting an artificial leg to a prosthesis mounting part, the hip joint comprising:

an upper transverse link having on its upper side a connector for attachment to a prosthesis mounting part:
a lower transverse link having on its underside a connector for releasable attachment to an artificial leg;
a front link articulated at its upper section, via a first joint, to a front section of the upper transverse link and articulated at its lower section, via a third joint connection, to a front section of the lower transverse link, wherein the first and third joint connections together have at least five degrees of freedom;
a rear link articulated at its upper section, via a second joint connection, to a rear section of the upper transverse link and at its lower section, via a fourth joint connection, to a rear section of the lower transverse link,
wherein the second joint connection comprises a hinge pin having its pivot axis approximately perpendicular to the sagittal plane and has one degree of freedom, and
wherein the fourth joint connection has a pivot axis with mediolateral and anteroposterior inclination with respect to the sagittal plane and has one degree of freedom, whereby a swiveling about the pivot axis of the second joint connection causes outward/inward swiveling and abduction/adduction of the lower transverse link; and
an extension limit stop defining the starting position of the hip joint in extension.

2. A hip joint as claimed in claim 1, wherein the first and third joint connections each comprise a spherical joint.

3. A hip joint as claimed in claim 1, wherein the first and third joint connections each comprise a cardan joint, and wherein the front link which connects the joints is pivotable about its longitudinal axis.

4. A hip joint as claimed in claim 1, further comprising means for varying the distance between the first and third joint connections.

5. A hip joint as claimed in claim 4, wherein the distance varying means includes means associated with the front link for varying its length.

6. A hip joint as claimed in claim 1, wherein the front link is elastic in the direction of tension.

7. A hip joint as claimed in claim 1, wherein the extension limit stop comprises an elastically resilient member.

8. A hip joint as claimed in claim 7, wherein the extension position is defined by the length of the resilient member.

9. A hip joint as claimed in claim 8, wherein the resilient member functions as a storage spring.

10. A hip joint as claimed in claim 1, wherein the pivot axis of the fourth joint connection, viewed from the front, has an inclination of approximately 17°–18°.

11. A hip joint as claimed in claim 1, wherein the pivot axis of the fourth joint connection, viewed from above, has a skewed position of approximately 17°.

* * * * *